(12) United States Patent
Qian et al.

(10) Patent No.: US 8,518,227 B2
(45) Date of Patent: Aug. 27, 2013

(54) NANOPORE-BASED NANOPARTICLE TRANSLOCATION DEVICES

(75) Inventors: Shizhi Qian, Edison, NJ (US); Ali Beskok, Chesapeake, VA (US)

(73) Assignee: Old Dominion University Research Foundation, Norflolk, VA (US)

(\*) Notice: Subject to any disclaimer, the term of this patent is extended or adjusted under 35 U.S.C. 154(b) by 0 days.

(21) Appl. No.: 13/233,180

(22) Filed: Sep. 15, 2011

(65) Prior Publication Data
US 2012/0097539 A1    Apr. 26, 2012

Related U.S. Application Data

(60) Provisional application No. 61/383,385, filed on Sep. 16, 2010.

(51) Int. Cl.
*G01F 1/64* (2006.01)

(52) U.S. Cl.
USPC ........... 204/451; 204/401; 204/454; 204/459; 205/778

(58) Field of Classification Search
USPC .......................... 204/401, 459; 977/700, 773
See application file for complete search history.

(56) References Cited

U.S. PATENT DOCUMENTS

| 6,627,067 | B1 * | 9/2003 | Branton et al. | 205/778 |
| 6,805,783 | B2 * | 10/2004 | Ohkawa | 204/454 |
| 7,081,189 | B2 * | 7/2006 | Squires et al. | 204/451 |
| 2003/0127329 | A1 * | 7/2003 | DeVoe et al. | 204/454 |
| 2006/0191831 | A1 * | 8/2006 | Hansford et al. | 210/143 |

\* cited by examiner

*Primary Examiner* — Luan Van
*Assistant Examiner* — Steven Rosenwald
(74) *Attorney, Agent, or Firm* — Novak Druce Connolly Bove + Quigg LLP

(57) ABSTRACT

A nanoparticle translocation device includes a first reservoir having a first reservoir electrode, a second reservoir having a second reservoir electrode, and at least one nanopore providing fluid communication between the first and second reservoirs. The device also includes one or more inner electrode portions on an inner wall of the nanopore and one or more outer electrode portions disposed on an outer wall of the nanopore. The device further includes at least one DC voltage supply for selectively applying a DC voltage to each of the first reservoir electrode, the second reservoir electrode, and the outer electrode layer, where the inner electrode portions, the outer electrode portions, and the nanopore are in a substantially coaxial arrangement.

12 Claims, 5 Drawing Sheets

NANOPORE-BASED NANOPARTICLE TRANSLOCATION DEVICES

CROSS-REFERENCE TO RELATED APPLICATIONS

This application claims priority to U.S. Provisional Patent Application Ser. No. 61/383,385, entitled "NANOPORE-BASED NANOPARTICLE TRANSLOCATION DEVICES" and filed Sep. 16, 2010, the contents of which are hereby incorporated by reference in their entirety.

FIELD OF THE INVENTION

The present invention relates to nanoparticle translocation, and more specifically to apparatus and methods for nanoparticle translocation using nanopores.

BACKGROUND

The cost of DNA sequencing is still generally too expensive for routine applications. For example, the estimated cost, including conventional instrumentation, sample preparation and labor, for sequencing a haploid human genome ranges from $100,000 to $1,000,000. Despite the costs involved, it is expected that the demand for sequence information will keep increasing.

One proposed solution has been to perform DNA sequencing using biomolecule or DNA nanoparticle translocation through a nanopore. Nanoparticle translocation is an active, robust, repeatable and controllable engineering approach that has both fundamental and practical significances in a large number of scientific fields including genetics, biochemistry, biophysics, chemistry, physiochemistry, biomedical science, clinic diagnostics, molecular biology, evolutionary biology, and anthropology.

With respect to DNA sequencing, nanopore translocation would be used as follows. First, a translocation device is provided, including first and second reservoirs and a nanopore providing fluid communication between the reservoirs. The first and second reservoirs are configured to include cathode and anode electrodes, respectively. Further, the reservoirs and nanopore are filled with an aqueous electrolyte. Second, the DNA of interest is introduced into the first reservoir. Third, a DC voltage is imposed across a nanopore submerged in an aqueous electrolyte, resulting in an ionic current through the nanopore and electrophoresis of the DNA through the nanopore. Finally, the ionic current during translocation is measured to ascertain the sequence for the DNA in the first reservoir.

In general, the current through such a nanopore is very sensitive to the size and shape of the nanopore. Therefore, if single bases or strands of DNA pass (or part of the DNA molecule passes) through the nanopore by electrophoresis, this can create a measurable change in the magnitude of the ionic current through the nanopore. This ionic current through the nanopore can be measured using conventional electrophysiological techniques. The ionic current is also affected by a DNA obstructing the nanopore and returns to a baseline current after the DNA exits the nanopore. In particular, since the A, C, G, and T nucleotides on a DNA molecule carry different surface charges, each nucleotide may alter the ionic current through the nanopore to a different characteristic degree. Accordingly, the amount of current which can pass through the nanopore at any given moment can vary depending on whether the nanopore is blocked by an A, a C, a G or a T nucleotide. Therefore, the change in the current through the nanopore as the DNA molecule passes through the nanopore represents a direct reading of the DNA sequence. As a result, it has been hypothesized that the sequence of bases in DNA can be recorded by monitoring such current modulations.

Although nanopore translocation-based DNA sequencing technologies appear to provide a solution for reducing costs of DNA sequencing, a practical system is still unavailable. A primary issue has been the lack of an ability to regulate the translocation process to achieve a nanometer-scale spatial accuracy. That is, the current resolution of ionic current detection systems is too low for the DNA translocation velocities. Accordingly, many efforts have focused on determining how to slow down DNA translocation through the nanopore by modifying viscosity, temperature, and voltage bias. However, such methods can result in a decrease of the signal to noise ratio, making detection of ionic currents difficult, or in a reduction of DNA attraction to the nanopore, thus lowering the overall throughput. Other efforts have focused on adjustment of equipment and/or the electrolyte, but methods typically require additional equipment or additional investigation.

SUMMARY

Embodiments of the invention concern systems and methods for nanoparticle translocation. In a first embodiment of the invention, a nanoparticle translocation device is provided. The device includes a first reservoir having a first reservoir electrode, a second reservoir having a second reservoir electrode, and at least one nanopore providing fluid communication between the first and second reservoirs. The device also includes one or more inner electrode portions on an inner wall of the nanopore, one or more outer electrode portions disposed on an outer wall of the nanopore, and at least one DC voltage supply for selectively applying a DC voltage to each of the first reservoir electrode, the second reservoir electrode, and the outer electrode layer. In the device, the inner electrode portions, the outer electrode portions, and the nanopore are in a substantially coaxial arrangement.

In a second embodiment of the invention, a nanoparticle translocation device is provided. The device includes a first reservoir having a first reservoir electrode, a second reservoir having a second reservoir electrode, and at least one nanopore providing fluid communication between the first and second reservoirs. The device also includes one or more inner electrode portions on an inner wall of the nanopore, one or more first joint electrode portions disposed along an inner surface of a first joint region for the first reservoir and the nanopore, and one or more second joint electrode portions disposed along an inner surface of a second joint region for the second reservoir and the nanopore. The device further includes at least one DC voltage supply for selectively providing a DC voltage signal between the first reservoir electrode and the second reservoir electrode, and at least one AC voltage supply for selectively providing a AC voltage signal between the first joint electrode portions and the second joint electrode portions. In the device, the inner electrode portions, the first and second joint electrode portions, and the nanopore are in a substantially coaxial arrangement.

In a third embodiment of the invention, a nanoparticle translocation device is provided. The device includes a first reservoir having a first reservoir electrode, a second reservoir having a second reservoir electrode, and at least one nanopore providing fluid communication between the first and second reservoirs. The device also includes one or more inner electrode portions on an inner wall of the nanopore and one or more outer electrode portions disposed on an outer wall of the nanopore. The device further includes one or more first joint electrode portions disposed along an inner surface of a first joint region for the first reservoir and the nanopore and one or more second joint electrode portions disposed along an inner surface of a second joint region for the second reservoir and the nanopore. Additionally, the device includes at least one DC voltage supply for selectively applying a DC voltage to each of the first reservoir electrode, the second reservoir electrode, and the outer electrode layer, and at least one AC voltage supply for selectively providing a AC voltage signal between the first annular electrode and the second annular electrode. In the device, the inner electrode portions, outer electrode portions, the first and second annular electrode portions, and the nanopore are in a substantially coaxial arrangement.

In a fourth embodiment of the invention, a method of translocating a nanoparticle in a first reservoir to a second reservoir. The method includes providing at least one nanopore to provide fluid communication of an electrolyte in the first and second reservoirs, the nanopore having one or more floating electrode disposed along an inner wall of the nanopore. The method also includes applying a DC voltage between the first and second reservoirs to draw the nanoparticle into the nanopore. The method further includes adjusting a velocity of the nanoparticle through the nanopore, responsive to drawing the nanoparticle into the nanopore, by applying at least one of an AC voltage between first and second ends of the nanopore and a DC voltage to the outer electrode of the nanopore.

DETAILED DESCRIPTION

Figure 1A:
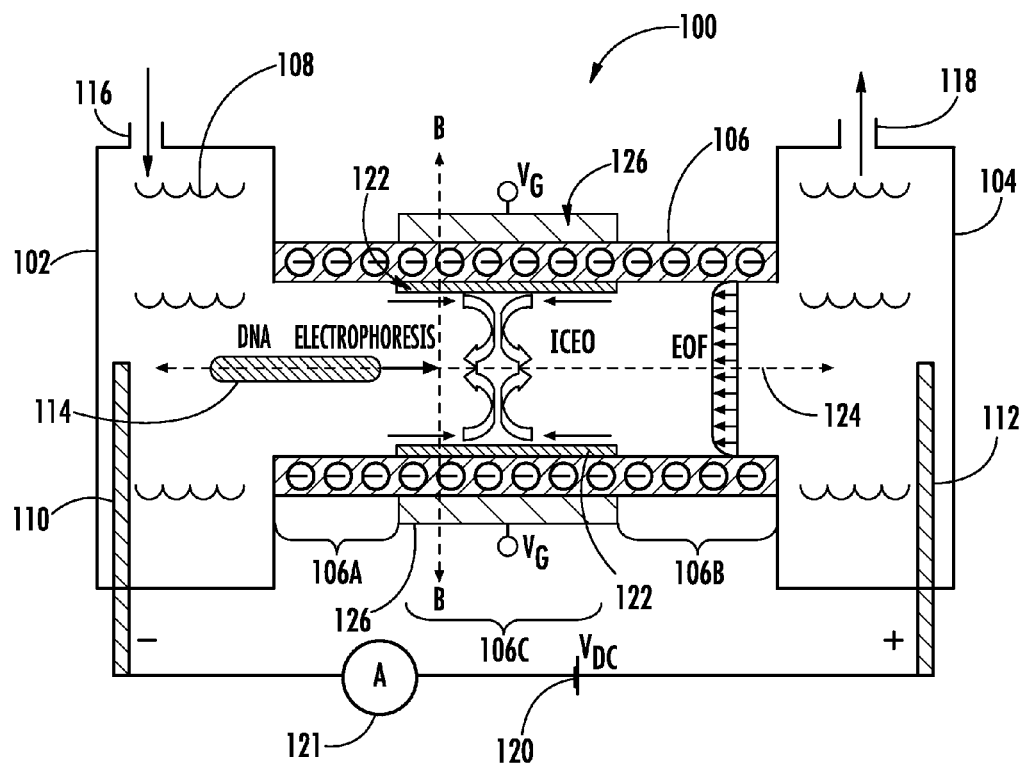
FIG. 1A shows a cross-section view of a first exemplary configuration of a nanoparticle translocation system in accordance with the various embodiments of the invention.

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

As described above, the primary challenge for implementation of low-cost nanopore translocation-based DNA sequencing technologies is providing an effective means for actively regulating DNA translocation through the nanopore. The various embodiments of the invention provide new systems and methods for actively regulating DNA translocation through a nanopore. In particular, the various embodiments of the invention provide new nanopore translocation device architectures that utilize a combination of floating and biased electrode portions (in addition to the conventional cathode and anode electrodes of the reservoirs) to actively regulate the translocation of DNA through the nanopore. In particular, the floating and biased electrode portions can be used to provide and/or adjust induced-charge electro-osmotic (ICEO) flow and electro-osmotic flow (EOF) in a nanopore.

As used herein, the term "nanopore" refers to any type of structure for directing fluids in which its interior dimensions are smaller than 100 nm. Accordingly, a nanopore includes both pore-type structures formed by an opening in a membrane and tube-type structures. Further, nanopores, as used herein, are not limited to cylindrical surface geometries and/or circular cross-sections. Thus a nanopore in the various embodiments of the invention can have a cylindrical or non-cylindrical surface geometry and/or a circular or non-circular cross-section.

In the various embodiments of the invention, the floating electrode portion is disposed along an inner wall of a electrically non-conductive nanopore in a substantially coaxial arrangement with the walls of the nanopore and is used to provide ICEO flow to passively slow down the particle motion. The biased electrode portions can be configured in a variety of ways. In some configurations, a gate electrode portion can be disposed along an outer wall of the nanopore in a substantially coaxial arrangement with the walls of the nanopore and can be used to adjust the EOF and to further adjust the ICEO flow in the nanopore. In other configurations, ring or annular-type electrodes can be provided along or near a joint region of the nanopore for each of the reservoirs and can be used to adjust the ICEO flow in the nanopore. In yet other configurations, a combination of different types of biased electrode portions can be used.

Mathematical Model of Nanoparticle Translocation Through a Nanopore

Prior to describing specific embodiments of the invention, the theoretical underpinnings of DNA translocation through a nanopore will be described. The underlying mechanism of DNA translocation is recognized as the interplay between ionic screening and hydrodynamics. A continuum model describing this interplay has revealed remarkable agreements with experimental measurements including translocation time, translocation velocity and force. Further, experiments have showed that DNA molecule was elongated or stretched after capture by the nanopore. Thus it is reasonable to approximate DNA molecule as a nanorod during the translocation process which is also justified by fair comparison between experiments and model predictions a posteriori. Molecular simulations could be used to further refine the results from the continuum model but the effects described by the continuum model should still remain, judging from the reasonable agreement with experiments. Importantly, explicit relations between the translocation velocity and various conditions (e.g., bulk concentration, nanopore dimension and the electric field intensity) or scaling law can be easily determined by the continuum model. Such information is important to understand the DNA translocation through a nanopore and further provides a knowledge base for rational design of experiments. Therefore, a continuum model taking into account the full interactions among the fluid flow, ionic mass transport, and particle motion is described as follows.

Continuum multi-ion model for fluid flow and ionic mass transport. The motion of an incompressible, Newtonian electrolyte solution is described by the Navier-Stokes equations:

$$\nabla \cdot u = 0, \quad (1)$$

$$\rho\left(\frac{\partial u}{\partial t} + u \cdot \nabla u\right) = -\nabla p + \mu \nabla^2 u - \rho_e \nabla \phi, \quad (2)$$

where $\rho_e = F \sum_{i=1}^{K} z_i c_i$ is the net charge density, $c_i$ is the molar concentration, $z_i$ is the valance of the $i^{th}$ ionic species, F represents the Faraday's constant, K is the total number of species in the solution, u is the velocity vector, p is the pressure, $\rho$ and $\mu$ are the density and viscosity of the fluid, respectively, and t is the time.

No slip boundary condition is imposed on rigid walls of the reservoirs. Normal flow with pressure p=0 is applied to both ends of the two reservoirs. On the surface of the DNA molecule, neglecting the Stern layer, the fluid velocity is $u_p + w_p \times (x_p - X_p)$, where $u_p$ and $w_p$ are the translational and rotational velocities of the particle, respectively; $x_p$ and $X_p$ are the position vectors of the surface and the center of the particle.

The electric potential in the electrolyte solution, $\phi$, and ionic concentrations are governed by the Poisson-Nernst-Planck (PNP) equations:

$$-\in \nabla^2 \phi = \rho_o, \quad (3)$$

$$\partial c_i/\partial t + \nabla \cdot N_i = 0, (i=1,2,\ldots,K). \quad (4)$$

The flux density, $N_i$, due to convection, diffusion, and migration is given by $$N_i = uc_i - D_i \nabla c_i - z_i(D_i/RT)Fc_i\nabla\phi, (i=1,2,\ldots,K), \quad (5)$$

where $D_i$ is the diffusion coefficient of the $i^{th}$ species, R is the gas constant, T is the temperature of the solution, and $\in$ is the permittivity of the fluid.

For the Poisson equation (3), surface charge boundary condition is imposed on the surfaces of the reservoirs and the DNA molecule. External potentials will be imposed at electrodes placed in the fluid reservoirs. Along the inner surface of the nanopore without gate and floating electrodes, surface charge boundary condition, $-\in \partial \phi/\partial n = \sigma_w$, is used. Along the inner dielectric wall of the nanopore with gate electrode, the following interface boundary condition is used:

$$\phi = \phi_d \text{ and } \in \partial \phi/\partial n - \in_d \partial \phi_d/\partial n = -\sigma_w, \quad (6)$$

where $\phi_d$ and $\in_d$ are, respectively, the potential and permittivity of the dielectric wall of the nanopore, n is the unit normal vector pointed toward the fluid medium, and $\sigma_w$ is the surface charge density of the nanopore wall. The potential within the dielectric wall of the nanopore, $\phi_d$, is governed by $\nabla^2 \phi_d = 0$ subjected to the boundary condition $\phi_d = V_G(t)$ along the gate electrode. Therefore, one can control the potential at the nanopore wall/liquid interface by controlling the gate potential $V_G(t)$ applied to the gate electrode. Along the ideally polarizable floating electrode, $\phi = A$, where the constant A is determined by the constraint of total induced-charge along the surface of the floating electrode, S, is zero: $\int_s (n \cdot \nabla \phi) ds = 0$.

For the set of the Nernst-Planck equations (4), zero normal flux (i.e., $n \cdot N_i = 0$) is imposed on the rigid walls of the nanopore and reservoirs. At both ends of the two big reservoirs connecting the nanopore, constant bulk electrolyte concentrations are imposed. Along the surfaces of the DNA molecule which is impervious to ions, $n \cdot N_i = (n \cdot uc_i)$ is imposed.

The DNA experiences both the hydrodynamic force, $F_H$, due to the fluid flow, and an electrostatic force, $F_E$. The translational motion of the DNA is governed by the Newton's 2nd law:

$$m_p du_p/dt = F_H + F_E = \int (\sigma^H \cdot n) d\Gamma + \int (\sigma^M \cdot n) d\Gamma, \quad (7)$$

where $\sigma^H = -pI + \mu(\nabla u + \nabla u^T)$ and $\sigma^M = \in EE - \in (E \cdot E)I/2$ are the hydrodynamic stress tensor and the Maxwell stress tensor, E is the electric field intensity related to the electric potential by $E = -\nabla \phi$, $m_p$, and $\Gamma$ are, respectively, the mass and the surface of the DNA. The rotational motion of the DNA is described by:

$$d(I_p w_p)/dt = \int (x_p - X_p) \times (\sigma^H \cdot n + \sigma^M \cdot n) d\Gamma \quad (8)$$

where $I_p$ is the momentum of inertia matrix of the DNA molecule.

The centroid, $X_p$ and the orientation $\theta_p$ (three Euler angles) are governed by $$dX_p/dt = u_p \text{ and } d\theta_p/dt = w_p. \quad (9)$$

Initially, we assume that the DNA molecule is located in one of the fluid reservoirs and outside of the nanopore. The initial conditions for the fluid and DNA are:

$$u=0. \ u_p=0. \ \omega_p=0. \ X_p=X_{p0}. \ \theta_p=\theta_{p0}. \quad (10)$$

where $X_{p0}$ and $\theta_{p0}$ denote the initial location and orientation of the DNA molecule, respectively. It is recognized that governing equations for the DNA motion (eqs. 7-8), fluid flow (eqs. 1-2), electric field (eq. 3), and ionic concentrations (the set of eq. 4) are strongly coupled, and one can simultaneously solve all of them. In addition, the fluid domain varies with time due to the DNA nanoparticle motion.

Control of Nanoparticle Translocation

In view of the forgoing mechanisms of nanoparticle translocation inside a nanopore, that various embodiments of the invention propose the use of various additional electrodes to regulate, in real time, the speed and direction of motion of nanoparticles through nanopores. In particular, as described above, the various embodiments provide for the combination of a floating electrode and at least one additional electrode to control EOF and/or ICEO flow.

Figure 1B:
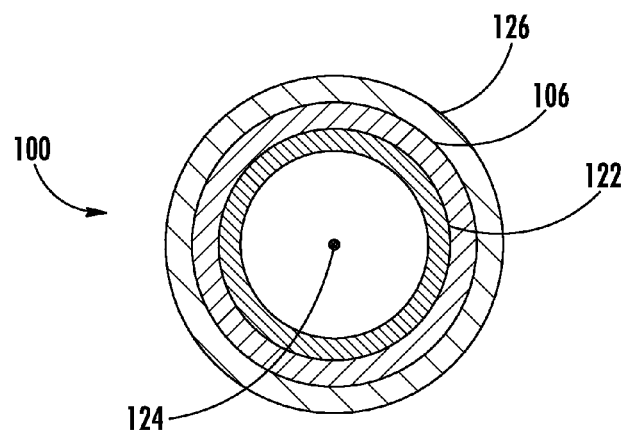
FIG. 1B shows a cross-section view the first exemplary configuration in FIG. 1A along cutline B-B in FIG. 1A.

Referring now to FIGS. 1A and 1B, there is shown a first exemplary configuration of a nanoparticle translocation system 100 in accordance with the various embodiments of the invention. FIG. 1A cross-section side view of system 100. FIG. 1B is a cross-section view of system 100 along cutline B-B in FIG. 1A.

As shown in FIG. 1A, the system 100 includes a first reservoir 102, a second reservoir 104, and a nanopore 106 providing a fluid connection between the reservoirs 102 and 104. In particular, nanopore 106 includes a first end section 106A, a second end section 106B (connected to reservoirs 102 and 104, respectively), and an intermediate section 106C in between. In the various embodiments of the invention, the nanopore 106 and reservoirs 102 and 104 are fabricated from electrically insulating or electrically semi-insulating materials. Further, the system includes an electrolyte 108 filled in reservoirs 102 and 104 extending through nanopore 106. Additionally, the system 100 includes a cathode electrode 110 disposed in reservoir 102 and an anode electrode 112 disposed in reservoir 104. In operation, the nanoparticles 114 to be translocated via the nanopore 106 can be introduced into first reservoir 102 via an inlet 116. Thereafter, any material reaching reservoir 104 can be removed via outlet 118. In operation, a DC voltage can be applied across electrodes 112 and 110 using a DC voltage supply 120 to cause an ionic current through the nanopore 106, inducing electrophoresis of nanoparticles in the first reservoir through the nanopore 106, and EOF of the electrolyte 108.

In addition to the components above, the system 100 also includes one or more floating electrode portions 122 disposed along the intermediate section 106C of nanopore 106. In particular, electrode portions 122 are disposed on an inner wall of the intermediate section 106C of nanopore 106, as shown in FIGS. 1A and 1B. Further, the floating electrode portions 122 are in a substantially coaxial relationship with nanopore 106, as shown in FIG. 1B. That is, electrode portions 122 and nanopore 106 are disposed about a same central axis 124 of nanopore 124.

In operation, when an external electric field induced by the DC power supply 120 via electrodes 110 and 112, the floating electrode portions 122 are polarized, inducing an equal and opposite surface charge on the floating electrode portions 122 and accordingly a non-uniform ICEO flow, schematically shown in FIG. 1A. Additionally, the voltage across electrodes 110 and 112 induces an ionic current, which can be monitored by an ammeter 121 or other current sensing device.

In the various embodiments of the invention, ICEO flow with opposing eddies is induced by the polarization of the floating electrode portions 122. The eddies consist of flow in a first direction at or near the floating electrode portions 122 and in a second direction at or near the centerline of the nanopore (i.e., the central axis 124). As a result, along central axis 124 and between floating electrodes 122 of the nanopore, the direction of the induced ICEO flow towards first reservoir 102 is opposite to that of the nanoparticle electrophoretic motion. Therefore, the induced ICEO flow retards the nanoparticle motion, and can be used to slow down nanoparticle translocation or even trap the particle inside the nanopore. In such configurations, the magnitude of the ICEO flow field is approximately proportional to the square of electric field intensity, which will be controlled by DC power supply 120 and electrodes 110 and 112.

Thus, the ICEO flow provides passive control of nanoparticle translocation via the floating electrode portions. That is, a variation in the DC voltage provided by supply 120, such as from 1 V to 3 V, can be applied to attract the nanoparticle into the nanopore 106. Once the nanoparticle 114 is attracted into nanopore 106 (which can be detected by a change in ionic current measured by ammeter 121), the nanoparticle motion is passively slowed down due to the strong ICEO flow formed near the floating electrode. In some instances, depending on the imposed DC electric field, which drives the nanoparticle into the nanopore 106 and induces ICEO flow near the floating electrode portions 112, the nanoparticle can be passively trapped inside the nanopore.

In FIGS. 1A and 1B, floating electrode portions 122 are shown as a single, annular electrode portion extending along an inner wall of nanopore 122 and along the length of intermediate section 106C. However, various embodiments of the invention are not limited in this regard. Rather, the electrode portions 122 can be formed using any number of electrode portions disposed about central axis 124, provided that that electrode portions are disposed in a substantially symmetric pattern about axis 124. Such an arrangement maintains to opposing eddies about central axis 124 for providing the ICEO flow shown in FIG. 1A.

To provide further control of the ICEO flow and the EOF, the embodiment in FIG. 1 also includes one or more gate electrode portions 126 disposed along the intermediate section 106C of nanopore 106. In particular, the gate electrode portions 126 are disposed on an outer wall of the intermediate section 106C of nanopore 106, as shown in FIGS. 1A and 1B. Further, the gate electrode portions 126 are in a substantially coaxial relationship with nanopore 106, as shown in FIG. 1B. That is, the gate electrode portions 126 and nanopore 106 are disposed about a same central axis 124 of nanopore 124.

System 100 operates as follows for a negatively charged nanoparticle 114. First, nanoparticles 114 are introduced into reservoir 102. Thereafter, the nanoparticles 114 are attracted from the first reservoir 102 into nanopore 106 via electrophoretic motion caused by the DC voltage applied across electrodes 110 and 112, as described above. As described above, attraction of the nanoparticle 114 into nanopore 106 can be detected by ammeter 121 via a change in the ionic current. Thereafter a gate potential, $V_G$, is applied at gate electrode portions 126. The applied gate potential results in an adjustment of ICEO and EOF, resulting in retardation or enhancement of the motion of nanoparticle 114 through nanopore 106.

The applied gate potential would result in adjustment of the ICEO in the nanopore 106 as follows. As described above, the floating electrode 122 is polarized to induce an ICEO flow when a DC voltage is applied across the electrodes 110 and 112. When the gate electrode 126 is floating (electrically isolated), the floating electrode 122 is "ideally polarized". That is, the floating electrode contains zero net induced charge (or zeta potential). As a result, the net ICEO flow (i.e., the spatially averaged ICEO flow) is zero. This net zeta potential along the interface of floating electrode/electrolyte can then be modulated by the gate potential, $V_G$, imposed to the gate electrode 126, via capacitive coupling. Accordingly, the overall double layer formed in the vicinity of the floating electrode 122 is the superposition of the standard IECO double layer (when the gate electrode 126 is floating) and the double layer induced by the gate potential via capacitive coupling. Thus, the overall ICEO is dependent on the amount of polarization on the floating electrode portions 122, the capacitance of the dielectric wall 106 located between the gate electrode 126 and the floating electrode 122, and the potential drop between the electrolyte in the vicinity of 122 and the gate electrode 126. Accordingly, the combination of the floating electrode portions 122 and gate electrode portions 126 provides two degrees of freedom for adjusting the ICEO flow.

The applied gate potential would result in adjustment of the EOF in the nanopore 106 as follows. When a negative gate potential is applied at gate electrode 126, the nanopore 106 becomes negatively charged and more cations (from electrolyte 108) are accumulated near the inner walls of nanopore 106, particularly in the vicinity of gate electrode portions 126. This accumulation provides an EOF opposite to the EOF caused by the DC voltage applied across electrodes 110 and 112, which retards the electrophoretic motion of the nanoparticle 114. In contrast, when a positive gate potential is applied at gate electrode 126, the nanopore 106 becomes positively charged and more anions (from electrolyte 108) are accumulated near the inner walls of nanopore 106, particularly in the vicinity of gate electrode portions 126. This accumulation provides an EOF in the same direction as the EOF caused by the DC voltage applied across electrodes 110 and 112, which enhances the electrophoretic motion of the nanoparticle 114.

It is worth noting that if the gate potential is applied prior to a nanoparticle 114 entering the nanopore 106, this can prevent the negatively charged nanoparticle 114 from entering the nanopore 106 if the DC voltage applied across electrodes 110 and 112 is relatively low. Thus, in order to attract nanoparticle 114 from the reservoir 102 into the nanopore 106 under a low voltage (e.g., between 0.1 V and 1.0 V), either no gate potential is initially applied or a positive gate potential is initially applied. As a result, formation of an opposing EOF is prevented (when gate electrode portions 126 are floating) or a cooperative EOF is formed (wherein $V_G > 0V$).

Once the nanoparticle 114 enters the nanopore 106, a negative gate potential (e.g., $-2.0V < V_G < 0$) is then applied at gate electrode portions 126 so that the direction of the EOF inside the nanopore 106 is opposite to that of the electrophoretic motion of the nanoparticle 114. The opposite EOF retards the electrophoretic motion of the nanoparticle 114 inside the nanopore. Under an appropriate magnitude of the gate potential and the electrical double layer thickness, the nanoparticle 114 can be trapped inside the nanopore.

In some configurations, the gate potential can be used to recapture the nanoparticle 114. As described above, the gate potential applied to gate electrode portions 126 controls the EOF in nanopore 106. Therefore, if a sufficient magnitude of the gate potential is provided, the EOF can dominate over the electrophoretic motion of the nanoparticle 114. Thus, this can cause the direction of motion of the nanoparticle 114 to be reversed. In the case of DNA sequencing, such a configuration would permit a single DNA nanoparticle to be analyzed multiple times.

In FIGS. 1A and 1B, gate electrode portions 126 are shown as a single, annular electrode portion extending along an outer wall of nanopore 106 and along the length of intermediate section 106C. However, various embodiments of the invention are not limited in this regard. Rather, the gate electrode portions 126 can be formed using any number of electrode portions disposed about central axis 124, provided that that such electrode portions are disposed in a substantially symmetric pattern about axis 124. Such an arrangement provides for a uniform adjustment of the EOF and the ICEO flow shown in FIG. 1A.

Figure 2A:
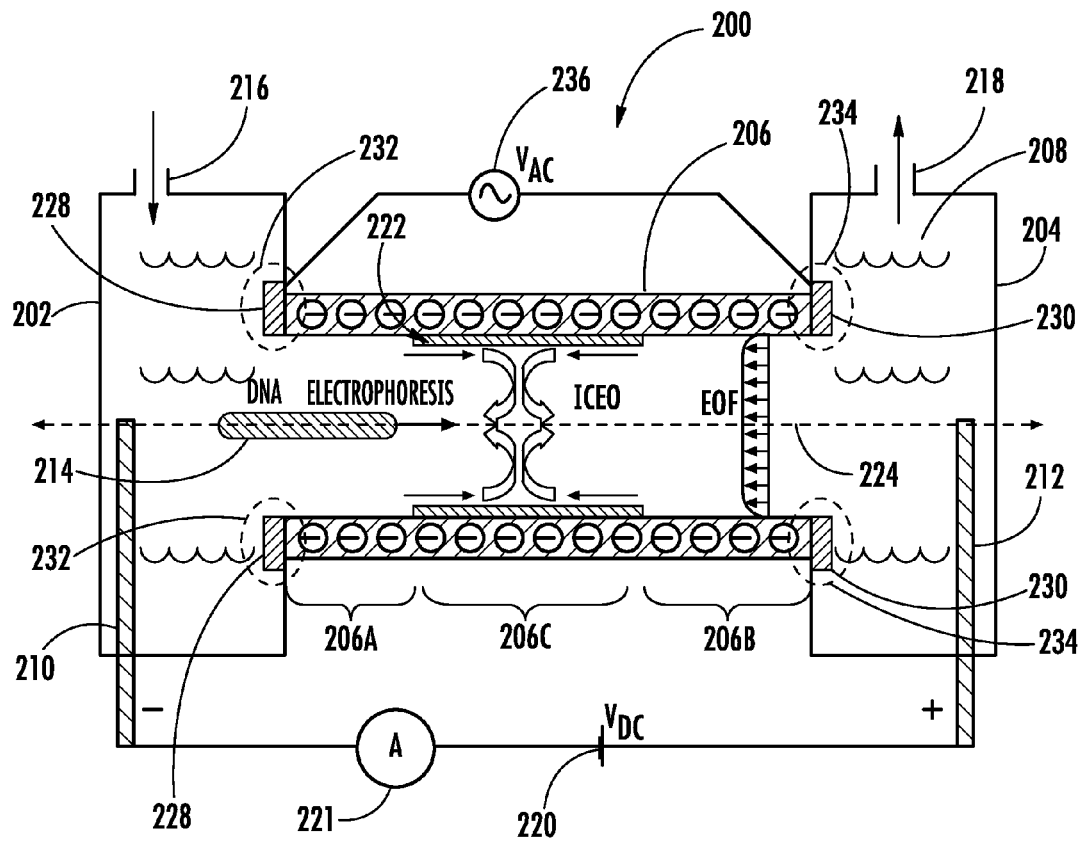
FIG. 2A shows a cross-section view of a second exemplary configuration of a nanoparticle translocation system in accordance with the various embodiments of the invention.
Figure 2B:
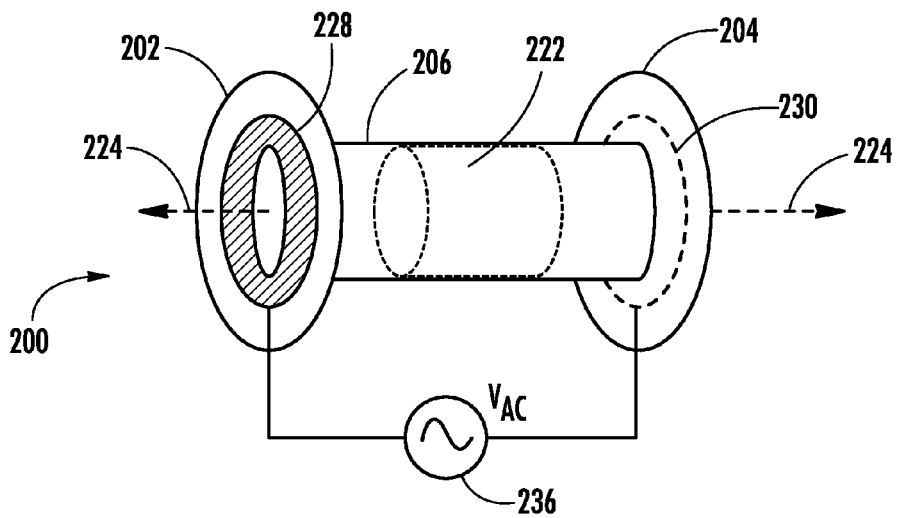
FIG. 2B shows a partial perspective view of the system in FIG. 2A.

Referring now to FIGS. 2A and 2B, there is shown a second exemplary configuration of a nanoparticle translocation system 200 in accordance with the various embodiments of the invention. FIG. 2A cross-section side view of system 200. FIG. 2B is a partial perspective view of system 200.

As shown in FIGS. 2A and 2B, system 200 for translocating a nanoparticle 214 includes a first reservoir 202, a second reservoir 204, a nanopore 206, and an electrolyte 208. The nanopore 206 includes end sections 206A and 206B, coupled to reservoirs 202 and 204, respectively, and an intermediate section 206C in between. The reservoirs 202 and 204 include a cathode electrode 210 and an anode electrode 212, respectively, and a DC voltage supply 220 coupled to electrodes 210 and 212. Further, the reservoirs 202 and 204 include an inlet 216 and an outlet 218, respectively, for introducing and extracting nanoparticle 214 in and out of system 200. Additionally, system 200 also includes floating electrode portions 222 and an ammeter 221 or other current sensing device for measuring ionic current. With respect to components 202-212 and 216-222, the configuration and operation of these components is substantially similar to that of components 102-112 and 116-122 in system 100. Accordingly, the description above for components 102-112 and 116-122 will be sufficient for describing the configuration and operation of components 202-212 and 216-222 in system 200.

In contrast to system 100, system 200 does not include a gate electrode portion. Instead, system 200 includes a first joint electrode 228 and a second joint electrode 230 at or near opposing ends of nanopore 206. In particular, the first joint electrode 228 is disposed along an inner wall of a first joint region 232 and about central axis 224 of system 200, where the first joint region 232 consists of portions of first end section 206A and adjacent portions of reservoir 202. The second joint electrode 230 is disposed along an inner wall of a second joint region 234, which consists of portions of second end section 206B and adjacent portions of reservoir 204. The joint electrodes 228 and 230 can then be used to apply an AC electric field generated by an AC power supply 236.

In FIGS. 2A and 2B, the joint electrodes 228 and 230 are shown as being at least primarily disposed on an inner wall of reservoirs 202 and 204, respectively. However, the various embodiments are not limited in this regard. Rather, the joint electrodes 228 and 230 can be disposed on any portions of joint regions 232 and 234, respectively. For example, joint electrodes 228 and 230 can extend partially onto the inner walls of sections 206A and 206B, respectively. In another example, the joint electrodes 228 and 230 can be primarily or completed disposed on the inner walls of sections 206A and 206B.

As described above with respect to system 100, the floating electrode portions 222 provides a means for passively controlling translocation of nanoparticle 214 via adjustment of the electric field imposed by DC supply 220 and electrodes 210 and 212. The addition of joint electrodes 228 and 230 and the AC signal provided by AC supply 236 provides a different method for providing active control of nanoparticle translocation. In particular, in addition to the DC voltage applied across electrodes 210 and 212, a small AC voltage signal, $V_{AC}$, at a high frequency can be applied across the two joint electrodes 228 and 230. For example, such signals can have a frequency at or above 1 kHz and amplitudes on the order of 1V.

Since the length of the nanopore 206 is on the order of ~100 nm and this defines the separation between joint electrodes 228 and 230, a high AC electric field can be generated using a relatively small AC signal. Further, the AC field at a very high frequency will not significantly affect the electrophoretic motion of the nanoparticle 214 or EOF in the nanopore 206. However, the AC electric field will affect the overall electric field intensity in the nanopore 206. Accordingly, since the strength of the induced ICEO flow is proportional to the square of the overall electric field intensity, the change in the overall electric field will cause changes in the strength of ICEO flow. Thus, by controlling the AC to DC field ratio, by adjusting $V_{AC}$ and $V_{DC}$ at supplies 236 and 220, respectively, the ICEO flow strength can be actively controlled. In particular, as the AC to DC field ratio is increased, the additional electric field due to the AC signal will increase ICEO flow. In contrast, as the AC to DC field ratio is decreased, the removal or reduction of the additional electric field due to the AC signal will decrease ICEO flow. When the ratio is zero (i.e., no AC signal), the ICEO flow will be reduced to its baseline ICEO flow (i.e., the ICEO flow due to the DC voltage alone).

In operation, before the nanoparticle 214 enters the nanopore 206, the AC to DC field ratio is reduced to zero to reduce the ICEO flow so that the nanoparticle 214 can be attracted from the reservoir 202 into the nanopore 206. At the same time, the resulting ionic current can be monitored via ammeter 221. Once a current drop is detected, indicating that a part of the nanoparticle 214 has entered the nanopore 206, the AC to DC field ratio can be increased to enhance the ICEO flow and slow down the nanoparticle translocation.

In FIGS. 2A and 2B, joint electrode portions 228 and 230 are each shown as single, annular electrode portions disposed in each of joint regions 232 and 234, respectively. However, various embodiments of the invention are not limited in this regard. Rather, each of the joint electrode portions 228 and 232 can be formed using any number of electrode portions disposed about central axis 224, provided that that such electrode portions are disposed in a substantially symmetric pattern about axis 224. Such an arrangement provides for a uniform adjustment of the electric field in the nanopore 206 and the ICEO flow shown in FIG. 2A.

Figure 3A:
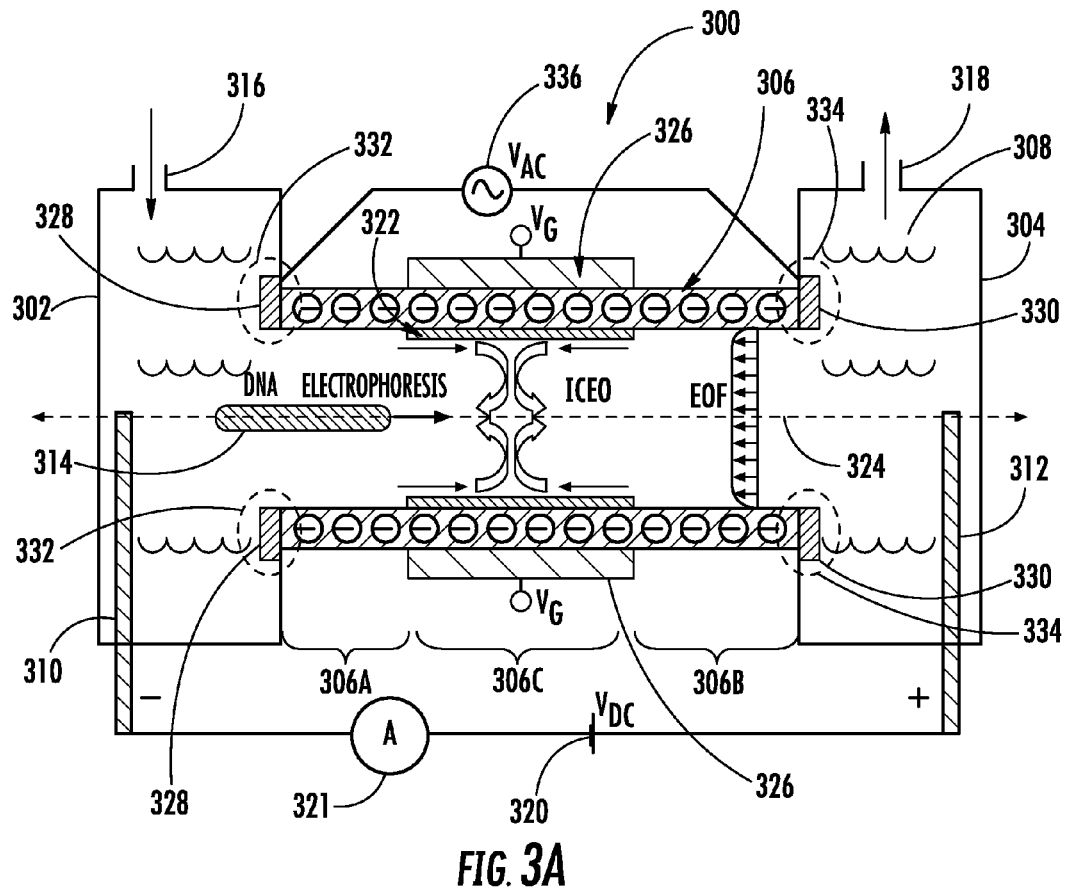
FIG. 3A shows a cross-section view of a third exemplary configuration of a nanoparticle translocation system in accordance with the various embodiments of the invention.
Figure 3B:
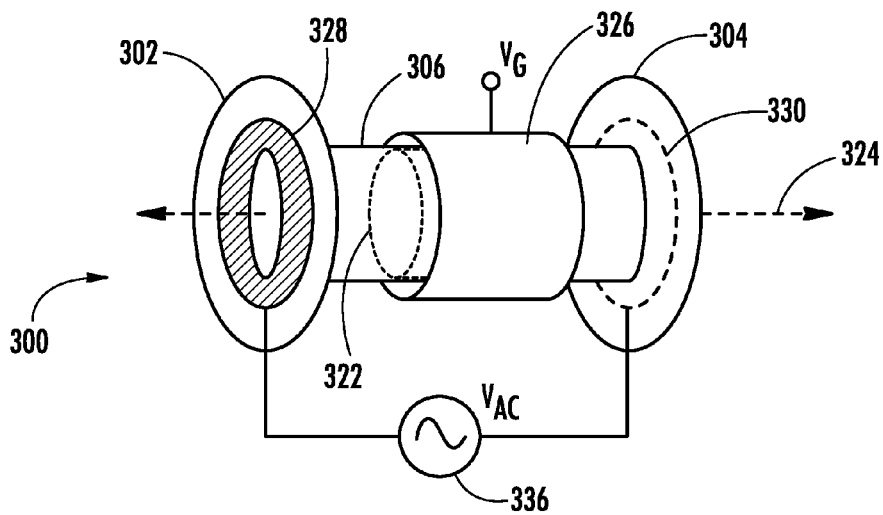
FIG. 3B shows a partial perspective view of the system in FIG. 3A.

Referring now to FIGS. 3A and 3B, there is shown a third exemplary configuration of a nanoparticle translocation system 300 in accordance with the various embodiments of the invention. FIG. 3A cross-section side view of system 300. FIG. 3B is a partial perspective view of system 300.

As shown in FIGS. 3A and 3B, system 300 for translocating a nanoparticle 314 includes a first reservoir 302, a second reservoir 304, a nanopore 306, and an electrolyte 308. The nanopore 306 includes end sections 306A and 306B, coupled to reservoirs 302 and 304 respectively, and an intermediate section 306C in between. The reservoirs 302 and 304 include a cathode electrode 310 and an anode electrode 312, respectively, and a DC voltage supply 320 coupled to electrodes 310 and 312. Further, the reservoirs 302 and 304 include an inlet 316 and an outlet 318, respectively, for introducing and extracting nanoparticle 314 in and out of system 300. Additionally, system 300 also includes floating electrode portions 322 and an ammeter 321 or other current sensing device for measuring ionic current. System 300 also includes gate electrode portions 326. Additionally, system 300 includes a first joint electrode portion 328 in joint portion 332 and a second joint electrode portion 330 in joint portion 334. Further, system 300 includes an AC voltage supply 336 coupled to electrodes 328 and 330.

With respect to components 302-312 and 316-322, the configuration and operation of these components is substantially similar to that of components 102-112 and 116-122 in system 100. Accordingly, the description above for components 102-112 and 116-122 will be sufficient for describing the configuration and operation of components 302-312 and 316-222 in system 300. With respect to components 326-336, the configuration and operation of these components is substantially similar to that of components 226-236 in system 200. Accordingly, the description above for components 226-236 will be sufficient for describing the configuration and operation of components 326-336 in system 300.

System 300 combines the various advantages of systems 100 and 200. That is, passive control of ICEO flow is provided via the combination of floating electrode portions 322 and the DC voltage applied across electrodes 310 and 312. Active control of ICEO flow can be provided via adjustment of the voltage potential, $V_G$, at gate electrode portions 326 and/or via adjustment of the AC signal, $V_{AC}$, at joint electrode portions 328 and 330. Thus, at least two degrees of freedom are provided for adjusting ICEO flow. Further active control of EOF can be provided via adjustment of the voltage, $V_G$, at gate electrode portions 326 and/or via adjustment of the DC signal, $V_{DC}$, at electrode portions 310 and 312. Thus, at least two degrees of freedom are also provided for adjusting EOF. Accordingly, once nanoparticle 314 is attracted into nanopore 306, independent or concerted adjustments of the AC signal, the DC signal, and the gate potential can be used to adjust the speed and position of the nanoparticle 314 in nanopore 306.

Fabrication of Nanoparticle Translocation Devices

Fabrication of devices in accordance with the various embodiments of the invention can be performed in various ways. For example, nanopore fabrication, as well as nanofluidic channel fabrication in sub-50 nm range and lower for various nanofluidic applications can be performed using laser-assisted micropipette pulling, lithography-based sacrificial spacers, lithography independent selective side etching of multilayer structures, nanoimprint lithography, ion track etching, drilling by focused electron beam, and nanoengraving via focused ion beam (FIB), to name a few. Amongst these methods FIB is tested to be very useful for drilling uniform nanopores in as low as sub-5 nm range with high degrees of precision. FIB methods can also be used to further functionalize the nanopores and can also be integrated with current state-of-the-art fabrication and characterization processes for further imaging and modification.

Figure 4:
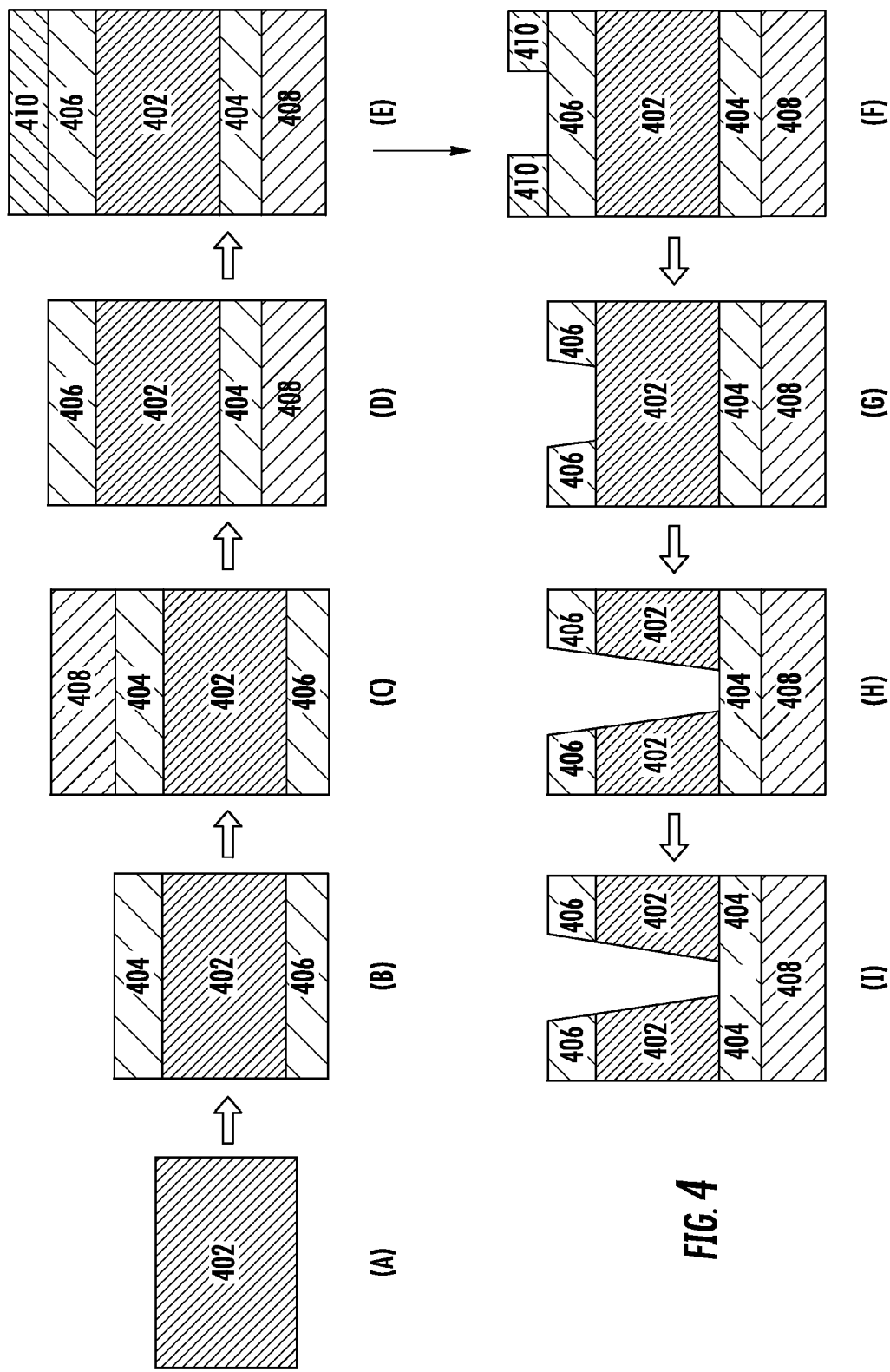
FIG. 4 is a series of cross-sections showing the various steps in an exemplary method for forming portions of a nanoparticle translocation device in accordance with the various embodiments of the invention.
Figure 5:
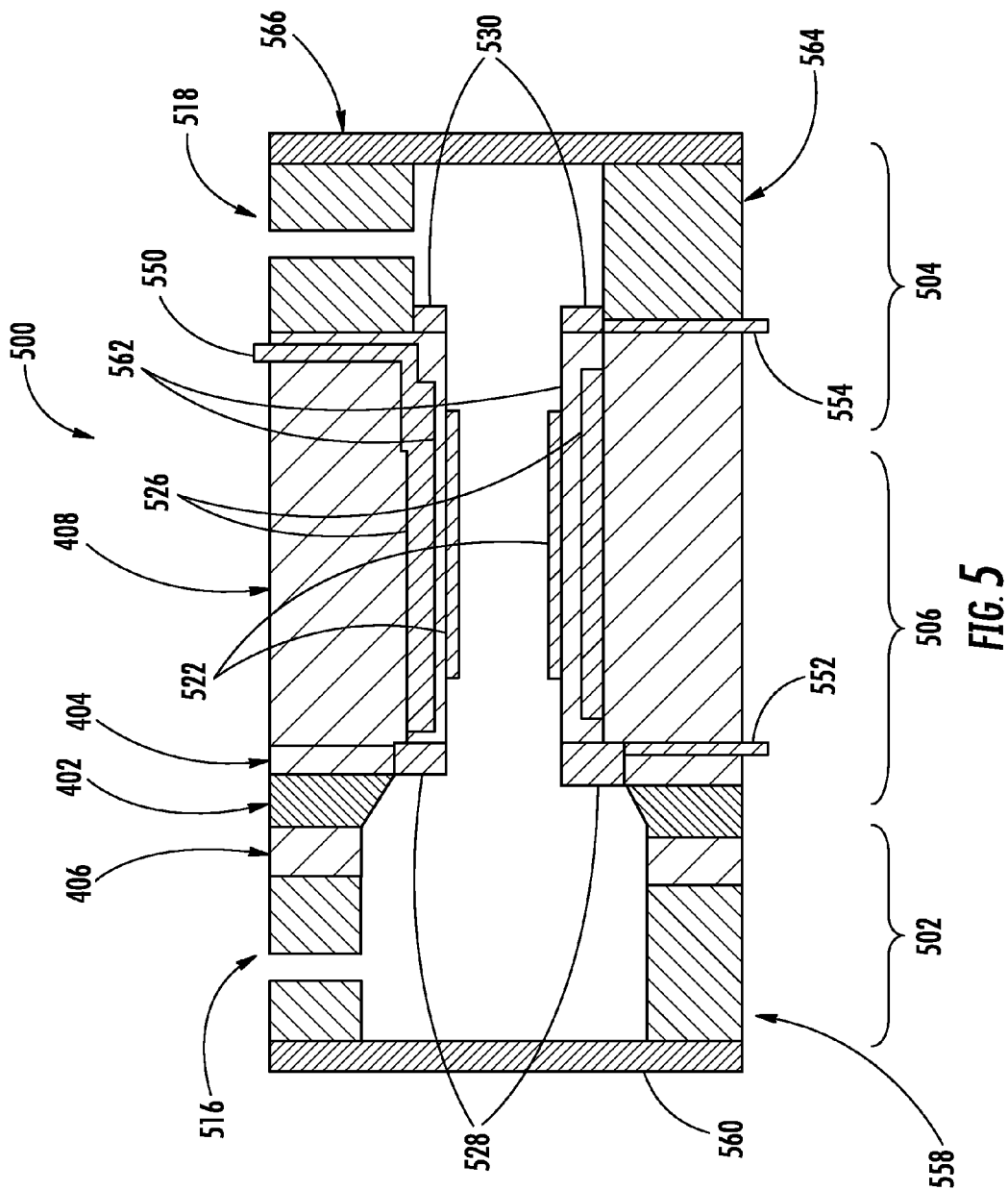
FIG. 5 is a cross-section view of a nanoparticle translocation device configured and fabricated in accordance with the various embodiments of the invention.

Referring now to FIGS. 4 and 5, one exemplary process for fabrication of a nanoparticle translocation device in accordance with the various embodiments of the invention will be described. In particular, an exemplary process for fabrication of a nanoparticle translocation device having a single nanopore of ~20 nm in diameter and ~100 nm in length, using a silicon carbide (SiC) membrane and FIB nanoengraving procedure, will be described. The fabrication process involves four major steps:

(1) SiC membrane is deposited in thin film form on an Si (100) wafer followed by UV lithographic pattering to define the nanopore through the membrane;
(2) FIB nanosculpting is used to engrave and open the nanopore within SiC membrane;
(3) FIB and/or atomic layer deposition (ALD) is used to deposit metallic and insulating layers within the nanopore to define the various electrodes;
(4) Reservoirs are created on both sides of the nanopore to form the final nanopore device.

Step I: Membrane Fabrication.

Although any materials can be used to form the membrane, some materials can be more advantageous with respect to the processes being used. For example, in the case of the membrane materials for FIB nanoengraving, substantially homogenous films having a low surface roughness allows uniform localization of ion beams during nanopore formation with good resolution. Also the film should be conductive (or at least semi-conductive) for dissipation of electrical charges transported by the incoming ions during patterning. Additionally, the film should be supportable by a sufficiently rigid substrate to allow manipulation during and after nanopore formation and practical device application.

Accordingly, silicon carbide (SiC) thin films possess properties that substantially meet the above-mentioned requirements. In particular, SiC can be deposited in ultra thin film form (>100 nm) with very good uniformity, low surface roughness (~1 Å) and with favorable electrical conduction properties to nullify the charging effect during ion engraving. The exemplary process provides for membrane fabrication is described below with respect to FIG. 4.

FIG. 4 is a series of cross-sections showing the various steps in an exemplary method for forming portions of a nanoparticle translocation device in accordance with the various embodiments of the invention. First, a Si (100) substrate 402 is provided (Step (a)). Thereafter, the substrate 402 can be oxidized to grow a frontside oxide layer 404 and a backside oxide layer 406 (Step (b)). For example, the substrate 402 can be oxidized at 950° C. to grow 250 nm silicon oxide layers on both sides of substrate 402. However, the various embodiments are not limited in this regard and any other type of electrically insulating materials can be used for forming layers 404 and 406. Thereafter, a SiC film 408 can be deposited on top of the frontside oxide layer 404 (Step (c)). The SiC film 408 can be deposited using various processes. For example, a 100 nm thick SiC film can be deposited using via magnetron sputtering with SiC target pellets. In this configuration, the backside oxide layer 406 will subsequently serve as an etch stop barrier during etch processes and the frontside oxide layer 404 is used to enhance the adherence of deposited SiC film 408. The generated strain on the wafer due to thin film formation can be adjusted by thermal treatment. Thus, the surface roughness can be reduced to as low as few nanometers.

After the layers are deposited, the Si substrate 402 and $SiO_2$ layers 404 and 406 are etched out from the backside of the substrate 402 up to the surface of the SiC film 408. Any type of lithographic technique can be used for this purpose. For example, the substrate 402 can be inverted (Step (d)) and a layer of photoresist 410 can be formed on backside oxide layer 406 (Step (e)). Thereafter, the photoresist layer 410 is patterned (Step (f)). This pattern can then be used to pattern the membrane opening from the backside oxide layer 406 through to the frontside oxide layer 404. That is, the pattern in photoresist layer 410 can be transferred first into backside oxide layer 406 (Step (g)). Thereafter, the pattern in backside oxide layer 406 can be used to form an opening through substrate 402 to frontside oxide layer 404 (Step (h)) and frontside oxide layer 404. For example, the lithography step can be followed by pattern transfer into backside oxide layer 404 layer via an etching technique, such as a reactive ion etching (RIE) technique. (Step (i)) The substrate can then be anisotropically wet-etched, using Tetramethylammonium hydroxide (TMAH) solution, for example. This can be followed by etching of the backside oxide layer 404 in ammonium fluoride solution. As TMAH etches Si much faster in <100> direction than <111> direction, a truncated pyramidal hole in the backside of the wafer will be formed. Thereafter, the nanopore can be formed using via FIB nanoengraving.

Step II: FIB Nanosculpting

In one exemplary configuration, the direct engraving of the SiC membrane can be done using a highly focused Ga+ beam having 5 to 60 keV energies. The full-width-at-half-maxima (FWHM) of the beam can be reduced to as low as 5 nm range with point dose as high as ~107 ions/point. The beam energy, beam width (FWHM), irradiation dose and drilling time can be configured to provide single nanopore with a diameter of approximately 60 nm. To minimize the re-deposition effect and increase the etching speed and nanopore uniformity, a gas-assisted FIB process can be used to locally injecting reactive gases in the immediate vicinity of the working area of the membrane to adsorb sputtered particle-forming volatile compounds and can be evacuated out.

Step III: Fabrication of Electrodes and Dielectric Layers within the Nanopore

Deposition of metallic electrodes and insulating layers for the nanopore can be done by two methods: (a) FIB writing and (b) ALD process. In a FIB writing method, the electrodes can be formed via selective deposition of electrically conductive and electrically insulating materials on the surface of the nanopore. In one configuration, platinum and silicon dioxide can be deposited by FIB to form the various electrodes described above. The FWHM of the ion beam and the pore diameter will determine the maximum allowance of the beam tip inside the pore and also define the electrode length. Thus, by varying the angle between the beam axis and the axis of the nanopore, and rotating the beam-tip along the surface of the nanopore, Pt layers can be formed.

For example, a process for system 100 or 300 is described below. In such systems, assuming a 5 nm thick Pt layer and 100 nm long nanopore with a 60 nm diameter, a gate electrode with an electrode length of around 80 nm inside the pore can be fabricated by either FIB or ALE process. Also a Pt line can be created that extends out of the nanopore for electrical contact and biasing the gate electrode. Thereafter, a dielectric layer (SiO2) can be deposited inside the nanopore to embed the gate electrode. This can be done via FIB-assisted deposition procedure. For example, a 60 keV Si+2 ion beam can be used from a liquid metal ion source (LMIS) consists of Au, Si and Be alloy source. A mixture of oxygen/tetramethoxysilane (TMS) precursor gas can then be used to deposit a silicon dioxide film on top of the gate electrode inside the nanopore. For example, a silicon dioxide film can be controlled to 10 nm. This deposition procedure is similar to that described for the Pt gate electrode.

The floating electrode can also be formed via a similar process as the Pt gate electrode. For example, in one embodiment, a Pt electrode of 5 nm thick and 50 nm in length can be deposited on the inner walls of the nanopore or top of a dielectric layer formed on the inner walls of the nanopore.

FIB writing can be again used to fabricate the joint electrodes. For example, two electrodes (50 nm wide and 10 nm thick) can be formed at the two ends of the nanopore, as shown above in systems 200 and 300. This process is similar to that described for the gate and floating electrodes.

Alternatively, ALD assisted electrode deposition can be used to form the various electrodes. For example, a 5 nm of Pt layer can be deposited inside the nanopore using (methylcyclopentadienyl)-trimethylplatinum (MeCpPtMe3) and oxygen as precursors followed by depositing 10 nm Al2O3 layer (using trimethyl aluminum, Al(CH3)3, and water as precursors) on top of the electrode to form the embedded gate electrode. Finally, a 5 nm floating electrode can be deposited in a similar way. Lastly, FIB writing can be used to fabricate the joint electrodes at the two ends of the nanopore.

Step IV: Fabrication of Reservoirs

Once the nanopore and the electrodes are defined, the reservoirs on both sides of the nanopore can be fabricated. For example, in one embodiment, the reservoirs can be formed in PDMS using the soft lithography technique. Briefly, masters containing the reservoir pattern, which is basically a microscale cylindrical pattern, can be created by spin-coating photoresist onto the substrate followed by soft baking, UV exposure, hard baking and development, leaving a positive relief containing the reservoir channel pattern. This process can include masking to preserve the contact vias for electrical connections and biasing of the electrodes.

Thereafter, liquid PDMS can be poured over the master and cured in a vacuum (e.g., 75° C. for 3-4 h). The negative PDMS cast of the reservoir channel pattern can then be removed from the master, and two holes can be punched from the side to serve as reservoirs' inlet and outlet. Immediately after plasma-treating, the PDMS cast and a glass slide can be bonded to get the desired reservoirs on both sides of the nanopore. The final device with embedded annular gate, annular floating and annular joint electrodes, as in system 300, along with reservoirs is schematically shown in FIG. 5.

FIG. 5 is a cross-section view of a translocation device 500 configured and fabricated in accordance with the various processes described above. Similar to system 300, device 500 includes a first reservoir portion 502 with an inlet 516, a second reservoir portion 504 with an outlet 518, and a nanopore portion 506. Further, the nanopore portion 506 includes a floating electrode portion 522 and a gate electrode portion 526. Additionally, device 500 includes annular joint electrode portions 528 and 530 disposed in reservoir portions 502 and 504, respectively.

In addition to the above-mentioned components, the device 500 also includes contact portions 550, 552, and 554. Contact portion 550 provides an electrical contact for applying a gate potential to gate electrode 526. Contact portions 552 and 554 provide electrical contacts to annular joint electrodes 528 and 530, respectively, for applying an AC electric field, as described above with respect to system 300.

First reservoir portion 502 consists primarily of the various layers from FIG. 4. That is, the reservoir portion 502 is defined by the opening in a stack of layers consisting of the backside oxide layer 406, the substrate 402, and the frontside oxide layer 404, as described above with respect to FIG. 4. Additionally, reservoir portion also includes a PDMS layer 558 and a glass layer 560, as described above, where inlet 516 is formed through PDMS layer 558.

The nanopore portion 506 consists primarily of the SiC film or membrane 408 described above with respect to FIG. 4. Further, the nanopore portion is processed to provide the various electrodes. For example, the FIB and/or ALD processing described above is used to define contact portion 550, gate electrode portion 526, a gate insulating layer 562, and floating electrode portion 522. Further, the FIB processing described above to form annular joint electrode portions 528 and 554 and their respective contact portions 552 and 554.

Reservoir portion 504 consists primarily of a PDMS layer 564 and a second glass layer 566, formed on the SiC layer 408 after electrodes are formed, as described above. Further reservoir 504 also includes an inlet 518 formed through PDMS layer 564.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments. For example, although an exemplary fabrication technique and arrangement of materials has been presented above, various other fabrication techniques and materials can be used in the various embodiments of the invention. Accordingly, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

What is claimed is:

1. A nanoparticle translocation device, comprising:
    a first reservoir having a first reservoir electrode;
    a second reservoir having a second reservoir electrode;
    at least one nanopore providing fluid communication between the first and second reservoirs;
    one or more inner annular electrode layers disposed on an inner wall of the nanopore;
    one or more outer annular electrode layers, separate from the inner electrode layers and disposed on an outer wall of the nanopore;
    and at least one DC voltage supply for selectively applying a DC voltage to each of the first reservoir electrode, the second reservoir electrode, and the outer annular electrode layers,
    wherein the inner annular electrode layers, the outer annular electrode layers, and the nanopore are in a substantially annular coaxial arrangement, and wherein the outer annular electrode layers overlie the inner annular electrode layers.

2. The device of claim 1, wherein the nanopore further comprises a first end section coupled to the first reservoir, a second end section coupled to the second reservoir, and intermediate section, and wherein the inner annular electrode layers and the outer annular electrode layers are disposed on the intermediate section of the nanopore.

3. The device of claim 1, wherein the outer annular electrode layers are configured to substantially overlie the inner annular electrode layers.

4. A nanoparticle translocation device, comprising:
    a first reservoir having a first reservoir electrode;
    a second reservoir having a second reservoir electrode;
    at least one nanopore providing fluid communication between the first and second reservoirs;
    one or more inner annular electrode layers disposed on an inner wall of the nanopore;
    one or more first joint electrodes, separate from the inner annular electrode layers and disposed along an inner surface of a first joint region for the first reservoir and the nanopore;
    one or more second joint electrodes, separate from the inner annular electrode layers and the first joint electrodes, disposed along an inner surface of a second joint region for the second reservoir and the nanopore;
    at least one DC voltage supply for selectively providing a DC voltage signal between the first reservoir electrode and the second reservoir electrode; and
    at least one AC voltage supply for selectively providing a AC voltage signal between the first joint electrode and the second joint electrode;
    wherein the inner annular electrode layers, the first and second joint electrodes, and the nanopore are in a substantially coaxial arrangement.

5. The device of claim 4, wherein the nanopore further comprises a first end section coupled to the first reservoir, a second end section coupled to the second reservoir, and intermediate section, and wherein the inner annular electrode layers are disposed on the intermediate section of the nanopore.

6. The device of claim 4, wherein at least a portion of the first joint electrode is disposed in portion of the joint region in the first reservoir, and wherein at least a portion of the second joint electrode is disposed in portion of the joint region in the second reservoir.

7. The device of claim 4, wherein the first joint electrode forms a first annular electrode, and wherein the second joint electrode forms a second annular electrode.

8. A nanoparticle translocation device, comprising:
a first reservoir having a first reservoir electrode;
a second reservoir having a second reservoir electrode;
at least one nanopore providing fluid communication between the first and second reservoirs;
one or more inner annular electrode layers disposed on an inner wall of the nanopore;
one or more outer annular electrode layers, separate from the inner electrode layers and disposed on an outer wall of the nanopore; and
one or more first joint electrodes disposed along an inner surface of a first joint region for the first reservoir and the nanopore;
one or more second joint electrodes disposed along an inner surface of a second joint region for the second reservoir and the nanopore;
at least one DC voltage supply for selectively applying a DC voltage to each of the first reservoir electrode, the second reservoir electrode, and the outer annular electrode layers; and
at least one AC voltage supply for selectively providing a AC voltage signal between the first joint electrode and the second joint electrode, wherein the inner annular electrode layers, outer annular electrode layers, the first and second joint electrodes, and the nanopore are in a substantially coaxial arrangement and wherein the outer annular electrode layers overlie the inner annular electrode layers.

9. The device of claim 8, wherein the nanopore further comprises a first end section coupled to the first reservoir, a second end section coupled to the second reservoir, and intermediate section, and wherein the inner annular electrode layers and the outer annular electrode layers are disposed on the intermediate section of the nanopore.

10. The device of claim 8, wherein the outer annular electrode layers are configured to substantially overlie the inner annular electrode layers.

11. The device of claim 8, wherein at least a portion of the first joint electrode is disposed in a portion of the joint region in the first reservoir, and wherein at least a portion of the second joint electrode is disposed in a portion of the joint region in the second reservoir.

12. The device of claim 8, wherein at least a portion of the first joint electrode forms a first annular joint electrode, and wherein at least a portion of the second joint electrode form a second annular joint electrode.

* * * * *